(12) United States Patent
Yamada

(10) Patent No.: US 8,520,797 B2
(45) Date of Patent: Aug. 27, 2013

(54) MEDICAL IMAGING APPARATUS, CONTROL METHOD, AND COMPUTER PROGRAM PRODUCT

(75) Inventor: Yasunobu Yamada, Nasushiobara (JP)

(73) Assignees: Kabushiki Kaisha Toshiba, Tokyo (JP); Toshiba Medical Systems Corporation, Otawara-shi (JP)

( * ) Notice: Subject to any disclaimer, the term of this patent is extended or adjusted under 35 U.S.C. 154(b) by 133 days.

(21) Appl. No.: 13/152,818

(22) Filed: Jun. 3, 2011

(65) Prior Publication Data

US 2011/0299656 A1    Dec. 8, 2011

(30) Foreign Application Priority Data

Jun. 3, 2010  (JP) ................. 2010-128253

(51) Int. Cl.
*G01N 23/00*    (2006.01)
(52) U.S. Cl.
USPC ............................. 378/4; 378/63
(58) Field of Classification Search
USPC ................................. 378/4–20, 63
See application file for complete search history.

(56) References Cited

U.S. PATENT DOCUMENTS

| 4,178,510 A | 12/1979 | Wagner |
| 5,412,215 A | 5/1995 | Shuto et al. |
| 6,490,476 B1 * | 12/2002 | Townsend et al. ............ 600/427 |
| 7,238,948 B2 | 7/2007 | Fritzler et al. |
| 7,795,590 B2 * | 9/2010 | Takahashi et al. ....... 250/363.03 |
| 2010/0046818 A1 | 2/2010 | Yamaya et al. |

FOREIGN PATENT DOCUMENTS

| CN | 1760694 A | 4/2006 |
| GB | 2 452 064 A | 2/2009 |
| JP | 2007-107995 | 4/2007 |
| JP | 2007-202976 A | 8/2007 |
| WO | WO 2008/120396 A1 | 10/2008 |

OTHER PUBLICATIONS

Chinese Office Action issued Jul. 17, 2012 in Patent Application No. 201110148062.3.

* cited by examiner

*Primary Examiner* — Hoon Song
(74) *Attorney, Agent, or Firm* — Oblon, Spivak, McClelland, Maier & Neustadt, L.L.P.

(57) ABSTRACT

A medical imaging apparatus includes an X-ray imaging apparatus; and a nuclear medicine imaging apparatus. The X-ray imaging apparatus includes an X-ray tube configured to emit X-rays for generating an X-ray CT image. The nuclear medicine imaging apparatus includes a detector configured to detect radiation for generating a nuclear medicine image. At least one of the X-ray imaging apparatus and the nuclear medicine imaging apparatus includes a determining unit configured to determine whether the detector detects the X-rays emitted by the X-ray tube, thereby determining whether there is a failure in the detector.

10 Claims, 7 Drawing Sheets

FIG.8

| MODULE ID | SCINTILLATOR NUMBER | ENERGY VALUE | DETECTION TIME |
|---|---|---|---|
| D1 | P11 | E11 | T11 |
| | P12 | E12 | T12 |
| | P13 | E13 | T13 |
| | ⋮ | ⋮ | ⋮ |
| D2 | P21 | E21 | T21 |
| | P22 | E22 | T22 |
| | P23 | E23 | T23 |
| | ⋮ | ⋮ | ⋮ |
| D3 | P31 | E31 | T31 |
| | P32 | E32 | T32 |
| | P33 | E33 | T33 |
| | ⋮ | ⋮ | ⋮ |
| ⋮ | ⋮ | ⋮ | ⋮ |

MEDICAL IMAGING APPARATUS, CONTROL METHOD, AND COMPUTER PROGRAM PRODUCT

CROSS-REFERENCE TO RELATED APPLICATION(S)

This application is based upon and claims the benefit of priority from Japanese Patent Application No. 2010-128253, filed on Jun. 3, 2010; the entire contents of which are incorporated herein by reference.

FIELD

Embodiments described herein relate generally to a medical imaging apparatus, a control method, and a computer program product.

BACKGROUND

In recent years, nuclear medicine imaging apparatuses, such as a gamma camera, a single photon emission computed tomography (SPECT) apparatus, and a positron emission tomography (PET) apparatus, have been known. The nuclear medicine imaging apparatus includes a detector that detects radiation. The nuclear medicine imaging apparatus detects radiation emitted from an isotope or a labeled compound which is introduced into body tissues using the detector and forms the image of the dose distribution of the radiation detected by the detector, thereby reconstructing a nuclear medicine image that provides the functional information of the body tissues.

For example, a radioactive drug including a labeled compound that is frequently introduced into tumor tissues is put into the body of the examinee. Then, the nuclear medicine imaging apparatus detects radiation emitted from the labeled compound for a predetermined period of time and reconstructs a nuclear medicine image including the distribution of the tumor tissues of the examinee into which the labeled compound is introduced.

In addition, in recent years, apparatuses have been proposed in which a nuclear medicine imaging apparatus that provides functional information is integrated with an X-ray computed tomography (X-ray CT) apparatus that provides shape information. For example, the following apparatuses have been proposed: a PET-CT apparatus in which a PET apparatus and an X-ray CT apparatus are integrated with each other; and a SPECT-CT apparatus in which a SPECT apparatus and an X-ray CT apparatus are integrated with each other.

When there is a failure in the detector of the nuclear medicine imaging apparatus, radiation is not detected. For example, there is a determination method that detects radiation emitted from a phantom including, for example, germanium(Ge)-68 and determines the detector that does not detect the radiation emitted from the phantom to be out of order.

However, the dose of radiation emitted from the phantom is small. Therefore, in the above-mentioned determination method, in some cases, it takes a long time to obtain a count required to determine whether there is a failure.

BRIEF DESCRIPTION OF THE DRAWINGS

FIG. 8 is a diagram of an example of count information stored in a storage unit according to the first embodiment;

DETAILED DESCRIPTION

According to one embodiment, a medical imaging apparatus includes an X-ray imaging apparatus; and a nuclear medicine imaging apparatus. The X-ray imaging apparatus includes an X-ray tube configured to emit X-rays for generating an X-ray CT image. The nuclear medicine imaging apparatus includes a detector configured to detect radiation for generating a nuclear medicine image. At least one of the X-ray imaging apparatus and the nuclear medicine imaging apparatus includes a determining unit configured to determine whether the detector detects the X-rays emitted by the X-ray tube, thereby determining whether there is a failure in the detector.

Hereinafter, as an example of a nuclear medicine imaging apparatus, a PET-CT apparatus will be described, but the embodiment is not limited thereto. For example, any apparatus, such as a SPECT-CT apparatus, may be used.

Figure 1:
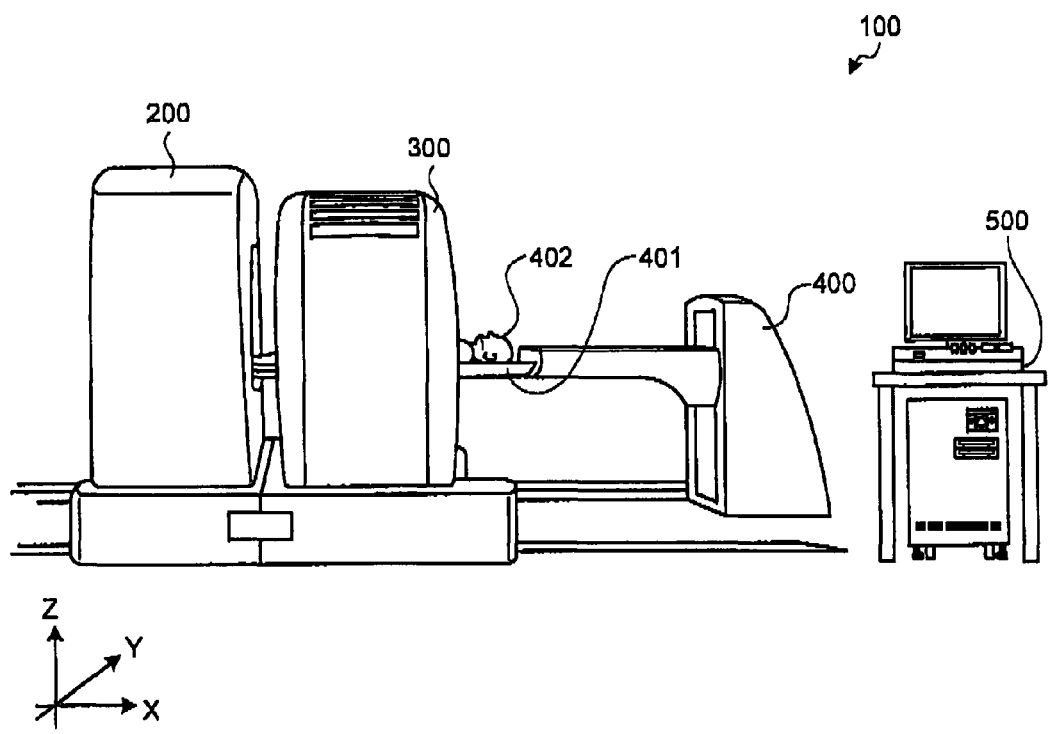
FIG. 1 is a diagram of the overall structure of a PET-CT apparatus according to a first embodiment.

FIG. 1 is a diagram illustrating the overall structure of a PET-CT apparatus according to a first embodiment. In FIG. 1, reference numeral 100 indicates a PET-CT apparatus, reference numeral 200 indicates a PET scanner, reference numeral 300 indicates an X-ray CT scanner, reference numeral 400 indicates a couch, reference numeral 401 indicates a top plate on which the examinee lies, and reference numeral 402 indicates the examinee. As shown in FIG. 1, the PET-CT apparatus 100 includes the PET scanner 200, the X-ray CT scanner 300, the couch 400, and a console 500. In FIG. 1, the X direction is the body axis direction of the examinee 402 who lies on the top plate 401 shown in FIG. 1. The Y direction is a direction on the horizontal plane that is orthogonal to the X direction. The Z direction is the vertical direction.

The couch 400 includes the top plate 401 on which the examinee 402 lies. Although not shown in FIG. 1, the couch 400 includes a couch control unit that moves the top plate 401. The couch control unit is controlled by the console 500 to move the examinee 402 on the top plate 401 into an imaging hole of the PET-CT apparatus 100.

The PET scanner 200 includes a plurality of detectors 210 that detects radiation for generating a nuclear medicine image. The detectors 210 are arranged in a ring shape around the body axis of the examinee 402. For example, the detectors 210 detect a pair of gamma rays emitted from a labeled compound that is put into the body tissues of the examinee 402 on the top plate 401, from the outside of the body of the examinee 402.

Specifically, whenever the detectors 210 detect the gamma rays, the PET scanner 200 collects a detection position indicating the position where the detector 210 detects the gamma rays, an energy value at the time when the gamma rays are incident on the detector 210, and the detection time when the detector 210 detects the gamma rays. The information collected by the PET scanner 200 is referred to as "count information."

Next, the relationship between the gamma rays detected by the detector 210 and a pair of gamma rays emitted from a labeled compound introduced into the body tissues of the examinee 402 will be described. The detector 210 does not always detect both a pair of gamma rays emitted from the labeled compound. For example, when a pair of gamma rays is emitted from the labeled compound, the detector 210 may detect only one of the pair of gamma rays, may detect both the pair of gamma rays, or may not detect any of the pair of gamma rays.

The labeled compound is, for example, 18F-labeled deoxyglucose that is labeled with "18F (fluorine)," which is a positron emitting nuclide. The labeled compound is given to the examinee 402 before measurement using the PET-CT apparatus 100. However, the labeled compound is not limited to the 18F labeled deoxyglucose, but any labeled compound may be used.

The X-ray CT scanner 300 includes an X-ray tube 301 that emits X-rays for generating an X-ray CT image and an X-ray detector 302 that detects the X-rays emitted by the X-ray tube 301. In the X-ray CT scanner 300, the X-ray tube 301 emits X-rays to the examinee 402 and the X-ray detector 302 detects the X-rays passing through the examinee 402. Specifically, while the X-ray CT scanner 300 is rotated about the body axis of the examinee 402, the X-ray tube 301 emits X-rays and the X-ray detector 302 detects the X-rays. That is, the X-ray CT scanner 300 emits X-rays to the examinee 402 in multiple directions while being rotated about the body axis of the examinee 402. The emitted X-rays pass through the examinee 402 and are absorbed by the examinee 402. As a result, the intensity of the X-rays is attenuated. The X-ray CT scanner 300 detects the attenuated X-rays. Data obtained by performing an amplification process or an A/D conversion process on the X-rays detected by the X-ray detector 302 is referred to as "projection data." The X-ray CT scanner 300 collects the projection data of the X-rays detected by the X-ray detector 302 and the detection position where the X-rays used to generate the projection data are detected.

Figure 2:
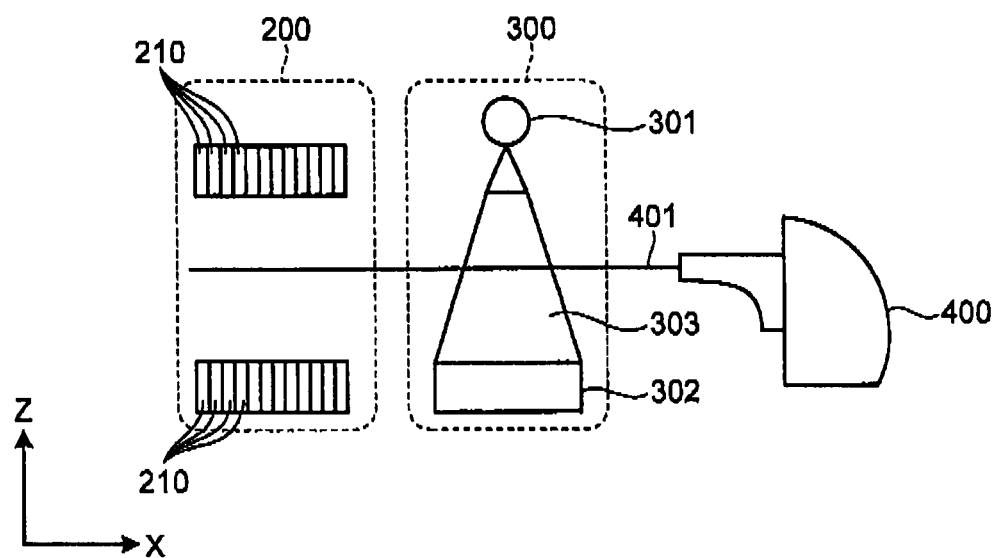
FIG. 2 is a diagram of an example of the relationship between a PET scanner and an X-ray CT scanner according to the first embodiment.

FIG. 2 is a diagram illustrating an example of the relationship between the PET scanner and the X-ray CT scanner according to the first embodiment. FIG. 2 is a cross-sectional view illustrating the PET scanner 200 and the X-ray CT scanner 300, as viewed from the Y-axis direction. In FIG. 2, reference numeral 200 indicates a PET scanner, reference numeral 210 indicates a detector, reference numeral 300 indicates an X-ray CT scanner, reference numeral 301 indicates an X-ray tube, reference numeral 302 indicates an X-ray detector, and reference numeral 303 indicates an X-ray emitted by the X-ray tube 301. For convenience of explanation, FIG. 2 shows the couch 400 and the top plate 401 in addition to the PET scanner 200 and the X-ray CT scanner 300.

As shown in FIG. 2, in the PET scanner 200, a plurality of detectors 210 is arranged in the X-axis direction. The plurality of detectors 210 is arranged so as to surround the body axis of the examinee 402 in a ring shape. As shown in FIG. 2, the X-ray CT scanner 300 includes the X-ray tube 301 and the X-ray detector 302. The X-ray tube 301 and the X-ray detector 302 are arranged so as to face each other with the top plate 401, on which the examinee 402 lies during measurement, interposed therebetween.

Figure 3:
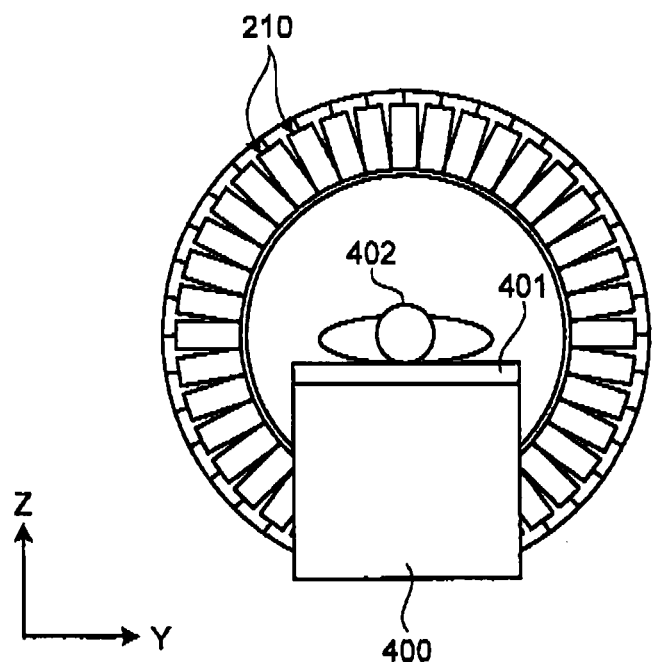
FIG. 3 is a diagram of the structure of the PET scanner according to the first embodiment.

FIG. 3 is a diagram illustrating the structure of the PET scanner according to the first embodiment. In FIG. 3, reference numeral 400 indicates a couch, reference numeral 401 indicates a top plate, reference numeral 402 indicates an examinee, and reference numeral 210 indicates a detector. FIG. 3 is a cross-sectional view illustrating the PET scanner, as viewed from the X-axis direction. For convenience of explanation, FIG. 3 shows the examinee 402, the couch 400, and the top plate 401 in addition to the PET scanner 200.

As shown in FIG. 3, in the PET scanner 200, a plurality of detectors 210 is arranged so as to surround the examinee 402 in a ring shape. The detector 210 is, for example, a photon counting type.

Figure 4:
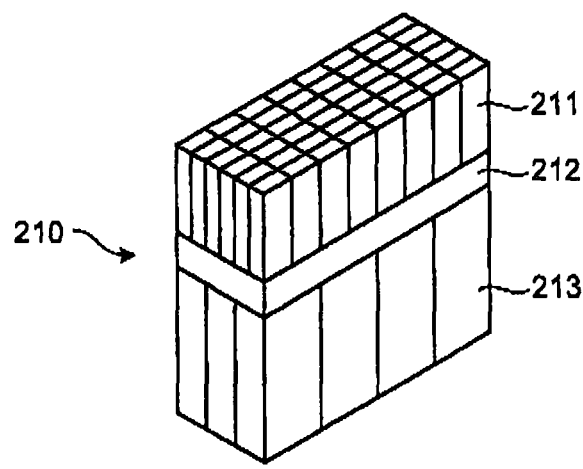
FIG. 4 is a diagram of an example of the structure of a detector according to the first embodiment.

FIG. 4 is a diagram illustrating an example of the structure of the detector according to the first embodiment. In FIG. 4, reference numeral 211 indicates a scintillator, reference numeral 212 indicates a light guide, and reference numeral 213 indicates a photomultiplier tube (PMT).

As shown in FIG. 4, the detector 210 includes the scintillator 211, the light guide 212, and the photomultiplier tube 213. The scintillator 211 converts the gamma ray that is emitted from the examinee 402 and is then incident on the detector 210 into visible light and outputs the visible light. The scintillator 211 is made of, for example, NaI or BGO that converts gamma rays into visible light. As shown in FIG. 4, the scintillators 211 are two-dimensionally arranged. The visible light output by the scintillator 211 is referred to as "scintillation light." The light guide 212 transmits the visible light output from the scintillator 211 to the photomultiplier tube 213. The light guide 212 is made of, for example, a plastic material having high light transmittance. The photomultiplier tube 213 receives the visible light output by the scintillator 211 through the light guide 212 and converts the received visible light into an electric signal. A plurality of photomultiplier tubes 213 is arranged.

Next, the photomultiplier tube 213 will be described. The photomultiplier tube 213 includes a photocathode that receives the scintillation light and generates photoelectrons, a multi-stage dynode that generates an electric field for accelerating the photoelectrons generated by the photocathode, and an anode which is an outlet through which electrons flow out. The electron emitted from the photocathode by the photoelectric effect is accelerated to the dynode and collides with the surface of the dynode. As a result, a plurality of electrons is ejected from the surface of the dynode. The phenomenon in which a plurality of electrons is ejected from the surface of the dynode is repeated over the multi-stage dynode and the number of electrons increases by geometrical progression.

For example, when receiving one scintillation light component, the anode outputs about 1,000,000 electrons. The number of electrons obtained from the anode when one scintillation light component is received is referred to as "the gain of the photomultiplier tube." In this case, the gain of the photomultiplier tube 213 is 1,000,000. In addition, a voltage of 1000 V (volt) or more is generally applied between the dynode and the anode in order to increase the number of electrons in geometrical progression.

As such, in the detector 210, the scintillator 211 converts the gamma ray into scintillation light and the photomultiplier tube 213 converts the visible light into an electric signal. In this way, the detector 210 detects the gamma ray emitted from the examinee 402.

Figure 5:
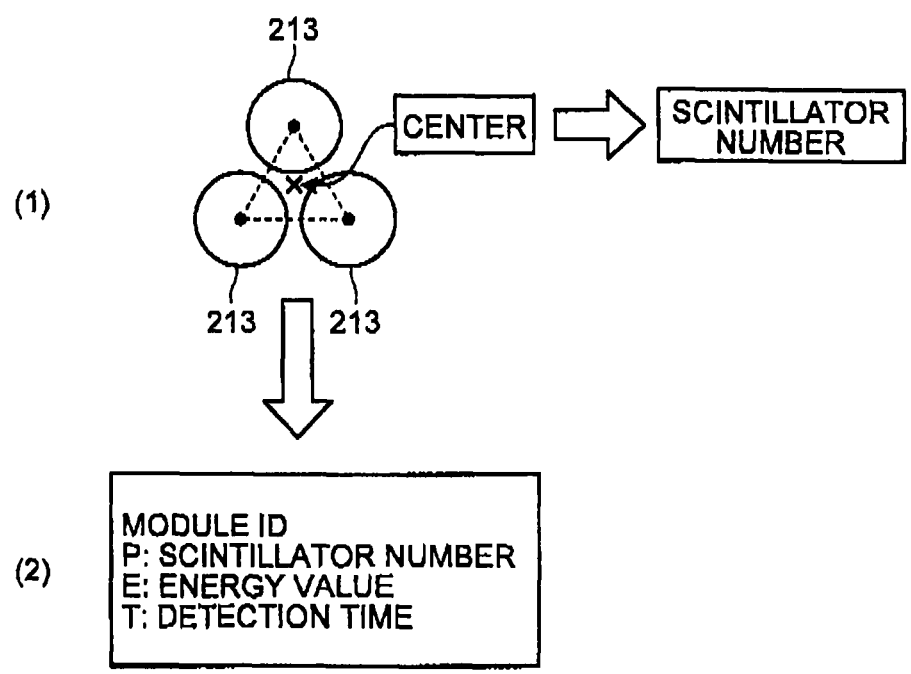
FIG. 5 is a diagram of information detected by an anger-type detector according to the first embodiment.

As described above, whenever the detector 210 detects the gamma ray, the PET scanner 200 collects the detection position, the energy value, and the detection time. Next, an example of a process of calculating the detection position and the energy value when a plurality of adjacent detectors 210 detect gamma rays at the same time will be described in brief with reference to FIG. 5. FIG. 5 is a diagram illustrating information detected by an anger-type detector according to the first embodiment.

For example, the PET scanner 200 performs an anger-type position calculating process to settle the detection position. For example, when the photomultiplier tube 213 is a position-detection-type photomultiplier tube, the PET scanner 200 collects the detection position using the position-detection-type photomultiplier tube 213. As shown in (1) of FIG. 5, a case in which three photomultiplier tubes 213 convert scintillation light into electric signals and output the electric signals at the same time will be described. In this case, the PET scanner 200 acquires the position of the photomultiplier tubes 213 that output the electric signals at the same time and acquires each of the energy values of the electric signals that are output from the photomultiplier tubes 213 at the same time. Then, the PET scanner 200 calculates the center position from the acquired energy values and specifies the scintillator 211 corresponding to the calculated center position. In addition, the PET scanner 200 integrates the energy values of the electric signals output from each of the photomultiplier tubes 213 that convert the scintillation light into electric signals and output the electric signals at the same time and uses the integrated energy value as the energy value of the gamma ray incident on the detector 210.

As shown in (2) of FIG. 5, whenever the detector 210 detects the gamma ray, the PET scanner 200 collects a "scintillator number" that uniquely identifies the scintillator 211, the "energy value," and the "detection time." In the example shown in (2) of FIG. 5, in addition to the "scintillator number," the "energy value," and the "detection time," a "module ID", which is information uniquely identifying the detector 210, is output.

The detection time may be absolute time, such as time, or the time elapsed from the start of the capture of a PET image. The detector 210 collects the detection time with an accuracy of, for example, 10 to 12 psec.

Figure 6:
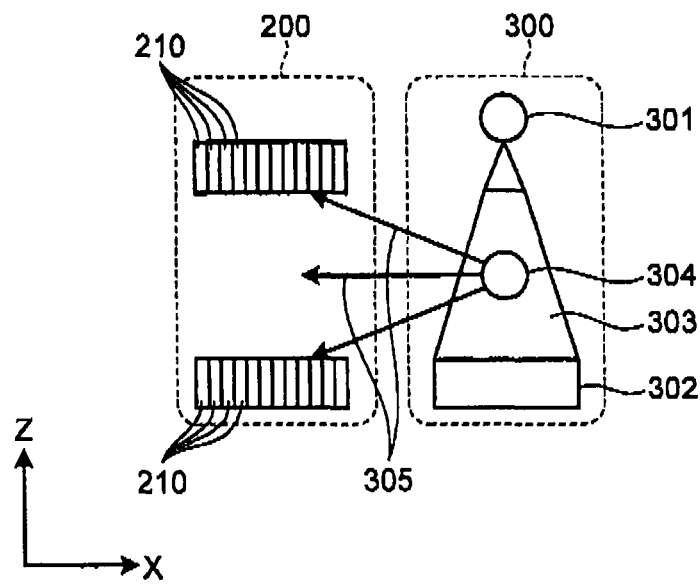
FIG. 6 is a diagram of a scatterer according to the first embodiment.

Next, returning to FIG. 1, the X-ray CT scanner 300 will be described. The X-ray CT scanner 300 includes a scatterer 304 that scatters an X-ray 303. FIG. 6 is a diagram illustrating a scatterer according to the first embodiment. In FIG. 6, reference numeral 304 indicates a scatterer and reference numeral 305 indicates an X-ray scattered by the scatterer 304. The X-ray scattered by the scatterer 304 is referred to as a "scattered X-ray." FIG. 6 is a cross-sectional view illustrating the PET scanner 200 and the X-ray CT scanner 300 according to the first embodiment, as viewed from the Y-axis direction.

As shown in FIG. 6, the scatterer 304 is arranged in the direction in which the X-ray tube 301 emits the X-ray 303. The scatterer 304 scatters the X-ray 303 emitted by the X-ray tube 301 such that a scattered X-ray 305 is incident on the detector 210 of the PET scanner.

When it is determined whether there is a failure in the detector 210 or when the failure position of the detector 210 is specified, the scatterer 304 is arranged in the direction in which the X-ray tube 301 emits the X-ray 303, which will be described below. For example, the scatterer 304 is provided on the top plate 401 at a position where the X-ray tube 301 emits the X-ray 303. However, the embodiment is not limited thereto. The scatterer 304 may not be provided on the top plate 401, may be suspended below the top plate 401, or may be arranged by any method. The scatterer 304 is not used when the X-ray CT image of the examinee 402 is captured.

The scatterer 304 may be made of any material capable of scattering the X-ray 303. For example, the scatterer 304 may be made of a metal material, such as iron. The scatterer 304 may have any shape as long as it can scatter the X-ray to the entire surface of the detector 210. For example, the scatterer 304 may be a sphere or a polyhedron, such as a mirror ball. The surface of the scatterer 304 may have an angle such that the X-ray is not scattered to the outside of the detector 210.

Next, the flow of a process when the PET-CT apparatus 100 according to the first embodiment reconstructs a PET image and an X-ray CT image will be described in brief. The PET scanner 200 and the X-ray CT scanner 300 are moved from the left to the right in FIG. 1 or FIG. 2, or the couch 400 is moved from the right to the left. The X-ray CT scanner 300 collects the projection data and then the PET scanner 200 collects the count information. Then, the console 500 reconstructs a PET image and an X-ray CT image on the basis of the collected information. However, the embodiment is not limited thereto. The PET scanner 200 and the X-ray CT scanner 300 may be moved from the right to the left in FIG. 1 or FIG. 2.

The console 500 corresponds to an information processing apparatus, such as a computer. The console 500 reconstructs an X-ray CT image using the projection data collected by the X-ray CT scanner 300. In addition, the console 500 generates coincidence information on the basis of the count information collected by the PET scanner 200 and reconstructs a PET image on the basis of the generated coincidence information. The console 500 is not described here, but will be described in detail below.

Figure 7:
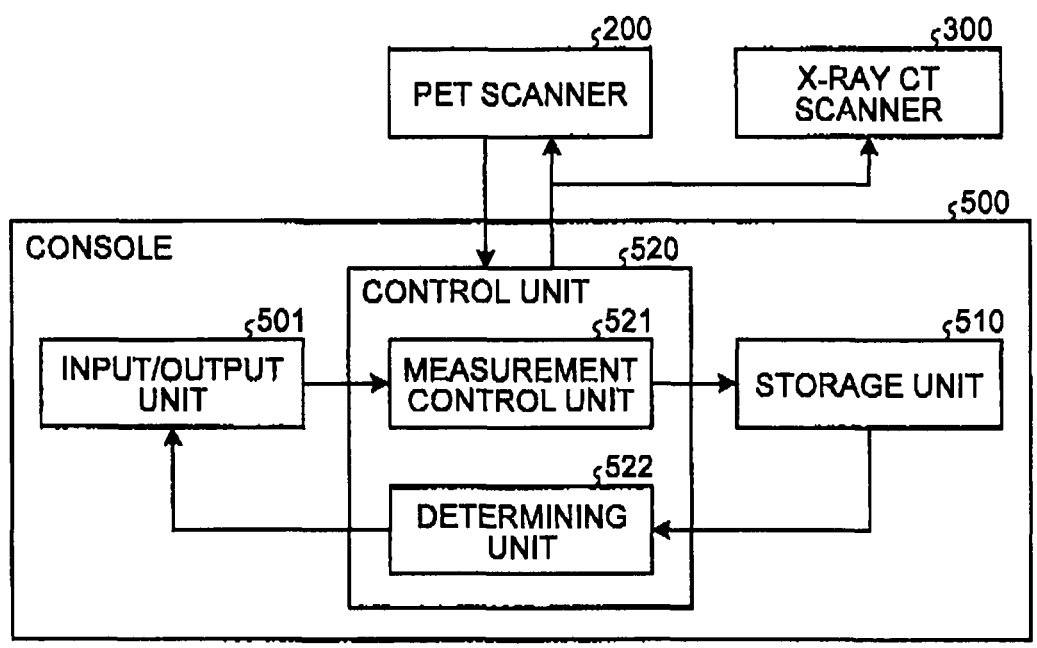
FIG. 7 is a block diagram of an example of the structure of a console according to the first embodiment.

FIG. 7 is a block diagram illustrating an example of the structure of the console according to the first. A process of reconstructing the PET image or the X-ray CT image using the console 500 may be performed by any method, which will be described in brief below.

The coincidence information will be described in brief. In a case in which a pair of gamma rays is emitted from the positron emitting nuclide and the detectors 210 detect both the pair of gamma rays, whenever the gamma rays are emitted from the positron emitting nuclide, the detectors 210 collect two count information items. The coincidence information indicates a combination of two count information items collected whenever the gamma rays are emitted from the positron emitting nuclide.

The console 500 specifies the detector 210 that is out of order, which will be described in detail below. For convenience of explanation, FIG. 7 shows the PET scanner 200 and the X-ray CT scanner 300 in addition to the console 500. In the example shown in FIG. 7, the console 500 includes an input/output unit 501, a storage unit 510, and a control unit 520.

The input/output unit 501 is connected to the control unit 520. The input/output unit 501 receives various kinds of instructions from the user of the PET-CT apparatus 100 and transmits the received instructions to the control unit 520. The input/output unit 501 receives information from the control unit 520 and outputs the received information to the user. For example, the input/output unit 501 is a keyboard, a mouse, a microphone, a monitor, or a speaker. A description of the details of the information or instruction received by the input/output unit 501 or the details of the information output by the input/output unit 501 will not be repeated here, but the details of the information or instruction will be described below together with each unit related thereto.

The storage unit 510 is connected to the control unit 520. The storage unit 510 stores data used in various kinds of processes of the control unit 520. The storage unit 510 is, for example, a semiconductor memory device, such as a random access memory (RAM) or a flash memory, or a storage device, such as a hard disk or an optical disk.

The storage unit 510 stores the count information collected by the PET scanner 200 when the X-ray CT scanner 300 emits X-rays. In the example shown in FIG. 8, the storage unit 510 stores a "scintillator number," an "energy value," and a "detection time" so as to be associated with a "module ID." FIG. 8 is a diagram illustrating an example of the count information stored in the storage unit according to the first embodiment.

In the example shown in FIG. 8, the storage unit 510 stores a scintillator number "P11," an energy value "E11," a detection time "T11," a scintillator number "P12," an energy value "E12," and a detection time "T12" so as to be associated with a module ID "D1." That is, the storage unit 510 stores that the scintillator "P11" of the detector "D1" detects a gamma ray with the energy value "E11" at the detection time "T11" and the scintillator "P12" of the detector "D1" detects a gamma ray with the energy value "E12" at the detection time "T12." In addition, the storage unit 510 stores information related to the other detectors 210 in the same way as described above.

The control unit 520 is connected to the input/output unit 501 and the storage unit 510. The control unit 520 includes an internal memory that stores programs for defining, for example, various kinds of procedures and controls various kinds of processes. The control unit 520 corresponds to an electronic circuit, such as an application specific integrated circuit (ASIC), a field programmable gate array (FPGA), a central processing unit (CPU), or a micro processing unit (MPU). In the example shown in FIG. 7, the control unit 520 includes a measurement control unit 521 and a determining unit 522.

When receiving a determination instruction to determine whether there is a failure from the user through the input/output unit 501, the measurement control unit 521 operates the PET scanner 200 and the X-ray CT scanner 300. Specifically, the measurement control unit 521 control the X-ray CT scanner 300 to start a process of emitting the X-ray 303. In this case, the measurement control unit 521 controls the X-ray tube 301 to start a process of emitting the X-ray 303 while being rotated about the body axis of the examinee 402. In addition, the measurement control unit 521 controls the PET scanner 200 to start a process of detecting radiation. Then, the measurement control unit 521 receives count information from the PET scanner 200 and stores the received count information in the storage unit 510.

The determining unit 522 determines whether the detector 210 detects the X-ray 303 emitted by the X-ray tube 301. When it is determined that the detector 210 does not detect the X-ray 303, the determining unit 522 determines that the detector 210 is out of order. When it is determined that the detector 210 detects the X-ray 303, the determining unit 522 determines that the detector 210 is normal.

Specifically, the determining unit 522 determines whether all of the scintillators 211 of the detector 210 detect radiation. More specifically, the determining unit 522 determines whether all of the scintillator numbers are included in the count information for each detector 210 with reference to the storage unit 510. When it is determined that not all of the scintillators 211 of the detector 210 detect radiation, the determining unit 522 determines that the detector 210 is out of order. When it is determined that all of the scintillators 211 of the detector 210 detect radiation, the determining unit 522 determines that the detector 210 is normal.

The determining unit 522 may specify a position where a failure occurs in detail. For example, the determining unit 522 may specify that the scintillator 211 specified by the scintillator number which is not included in the count information is out of order for the detector 210 that is determined to be out of order. Similarly, the determining unit 522 may specify that the light guide 212 which receives visible light output from the specified scintillator 211 is out of order, or it may specify that the photomultiplier tube 213 which receives visible light output from the specified scintillator 211 is out of order.

Figure 9:
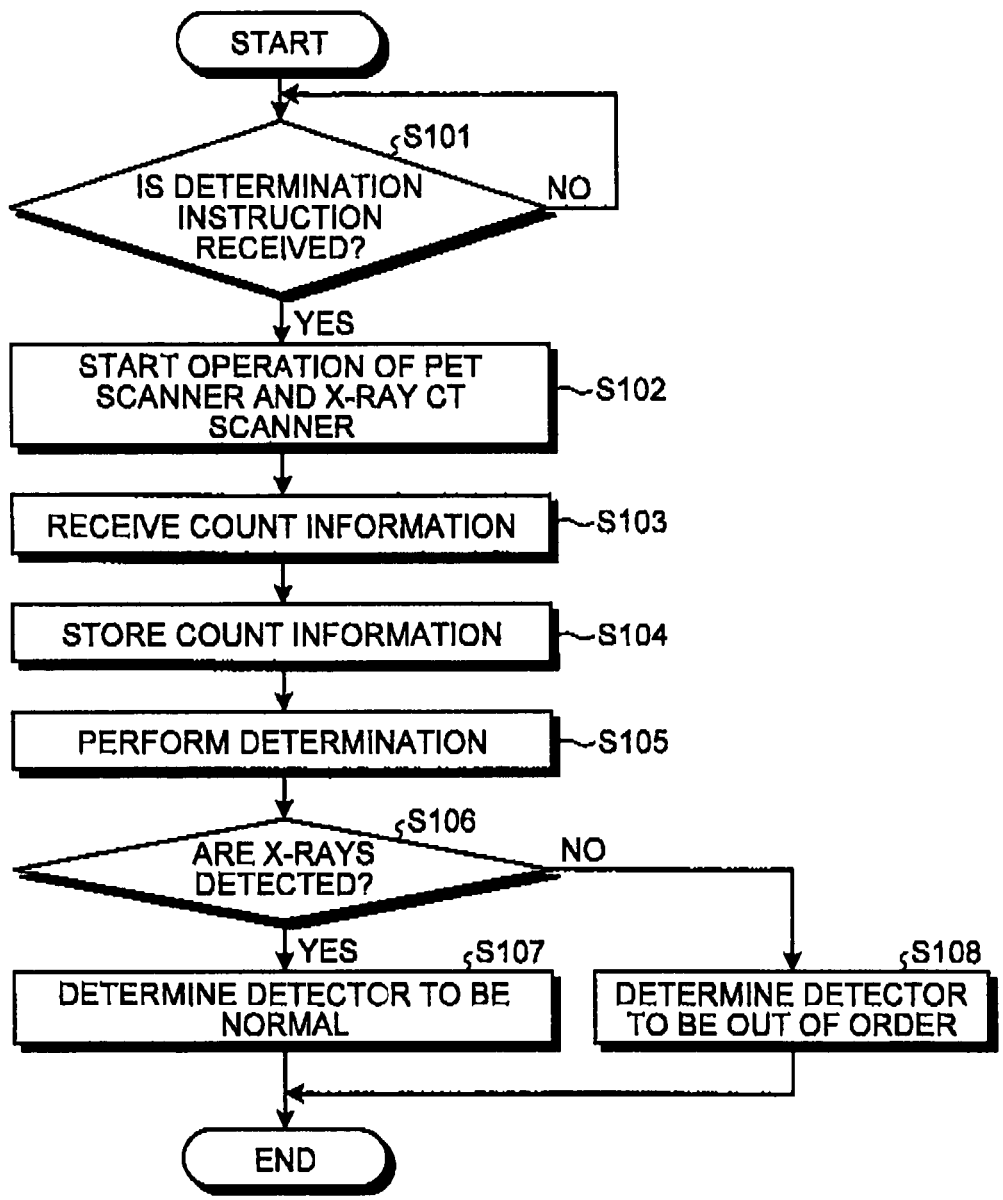
FIG. 9 is a flowchart of the flow of a determination process of the console according to the first embodiment.

Next, the flow of the determination process of the console 500 according to the first embodiment will be described with reference to FIG. 9. FIG. 9 is a flowchart illustrating the flow of the determination process of the console according to the first embodiment.

As shown in FIG. 9, when receiving a determination instruction to determine whether there is a failure from the user through the input/output unit 501 (Step S101: Yes), the measurement control unit 521 controls the PET scanner 200 and the X-ray CT scanner 300 to start their operations (Step S102). Then, the measurement control unit 521 receives count information from the PET scanner 200 (Step S103) and stores the received count information in the storage unit 510 (Step S104).

Then, the determining unit 522 determines whether the detector 210 detects the X-ray 303 emitted by the X-ray tube 301 (Step S105). When it is determined that the detector 210 does not detect the X-ray 303 (Step S106: No), the determining unit 522 determines that the detector 210 is out of order (Step S108). On the other hand, when it is determined that the detector 210 detects the X-ray 303 (Step S106: Yes), the determining unit 522 determines that the detector 210 is normal (Step S107).

As described above, according to the first embodiment, the PET-CT apparatus 100 includes the X-ray tube 301 that emits the X-ray 303 for generating an X-ray CT image and the detector 210 that detects radiation for generating a nuclear medicine image. The PET-CT apparatus 100 determines whether the detector 210 detects the X-ray 303 emitted by the X-ray tube 301. As a result, it is possible to obtain a count required to determine whether there is a failure in a short time and determine whether there is a failure in a short time.

That is, the dose of phantom used to check the operation of the detector 210 of the PET scanner 200 is small. When it is determined whether the detector 210 is out of order using radiation emitted from the phantom, it takes a long time to collect data. In addition, the does of radiation emitted from the phantom is attenuated over time. As a result, the time required to collect data further increases. In contrast, according to the first embodiment, it is determined whether there is a failure in the detector 210 using the X-ray 303 emitted from the X-ray CT scanner 300. The dose of X-ray emitted from the X-ray CT scanner 300 is several hundreds of times more than that of the phantom. According to the first embodiment, it is possible to determine whether there is a failure in a short time, as compared to the method using the phantom.

The X-ray CT scanner 300 can emit a predetermined dose of X-ray 303 at any time. As a result, according to the first embodiment, it is possible to prevent the imaging time from being affected by the attenuation of the dose of radiation, unlike the method using the phantom. In addition, according to the first embodiment, it is determined whether there is a failure using the scattered X-ray. However, as described above, the dose of X-ray emitted from the X-ray CT scanner 300 is several hundreds of times more than that of the phantom and it is possible to determine whether there is a failure in a short time even though the scattered X-ray is used, as compared to the method using the phantom.

According to the first embodiment, the PET-CT apparatus 100 further includes the scatterer 304 that is arranged in the direction in which the X-ray tube 301 emits X-rays and scatters the X-ray 303. The PET-CT apparatus 100 determines whether the detector 210 detects the X-ray that has been emitted by the X-ray tube 301 and then scattered by the scatterer 304.

As such, since the scatterer 304 scatters the X-ray 303 emitted by the X-ray CT scanner 300, it is possible to determine whether there is a failure in a short time using the X-ray 303 emitted by the X-ray tube 301 even though the X-ray emitted by the X-ray tube 301 is not directly incident on the detector 210.

According to the first embodiment, in the PET-CT apparatus 100, the X-ray tube 301 emits the X-ray 303 while being rotated about the space in which the examinee 402 is arranged. When the X-ray tube 301 is not moved, the scattered X-ray is not incident on all of the detectors 210. However, according to the first embodiment, since the X-ray tube 301 emits X-rays while being rotated, it is possible to reliably make the scattered X-ray incident on all of the detectors 210.

The first embodiment has been described above, but the embodiment is not limited thereto. The embodiment may be applied to embodiments other than the first embodiment. Next, other embodiments will be described.

For example, in the above-described embodiment, when the determination process is performed, the X-ray CT scanner 300 emits the X-ray 303 while being rotated. However, the embodiment is not limited thereto. For example, the X-ray CT scanner 300 may emit the X-ray 303 without being rotated.

Figure 10:
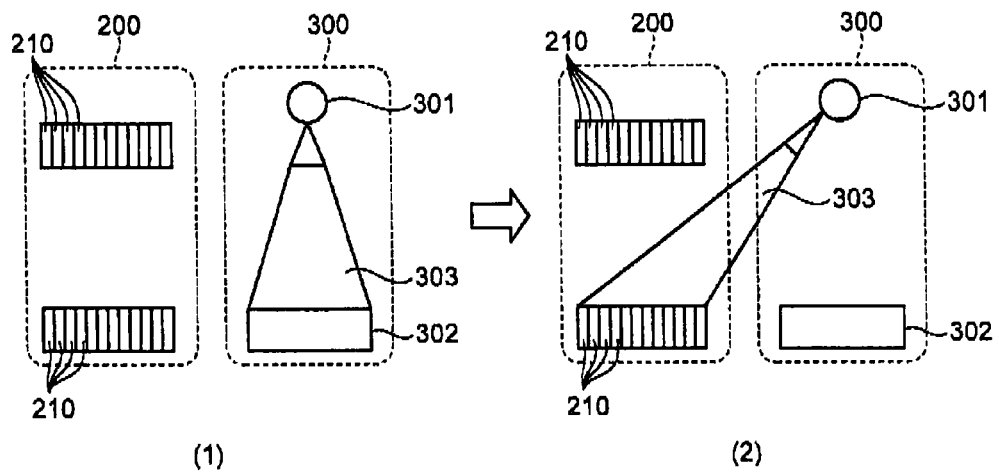
FIG. 10 is a diagram of a change in the direction in which an X-ray tube emits X-rays.

For example, in the above-described embodiment, the scatterer 304 is used, but the embodiment is not limited thereto. The scatterer 304 may not be used. For example, when the determination process is performed; the control unit 520 may adjust a collimator of the X-ray tube 301 to change the direction in which the X-ray 303 is emitted. FIG. 10 is a diagram illustrating a change in the direction in which the X-ray tube emits X-rays. (1) of FIG. 10 shows a state before the change in the direction and (2) of FIG. 10 shows a state after the change in the direction. As shown in (2) of FIG. 10, the control unit 520 changes the direction in which the X-ray tube 301 emits the X-ray 303 to the detector 210. Then, the control unit 520 controls the X-ray tube 301 to emit the X-ray 303 while being rotated about the space in which the examinee 402 such that the X-ray 303 is emitted to the entire surface of the detector 210.

Figure 11:
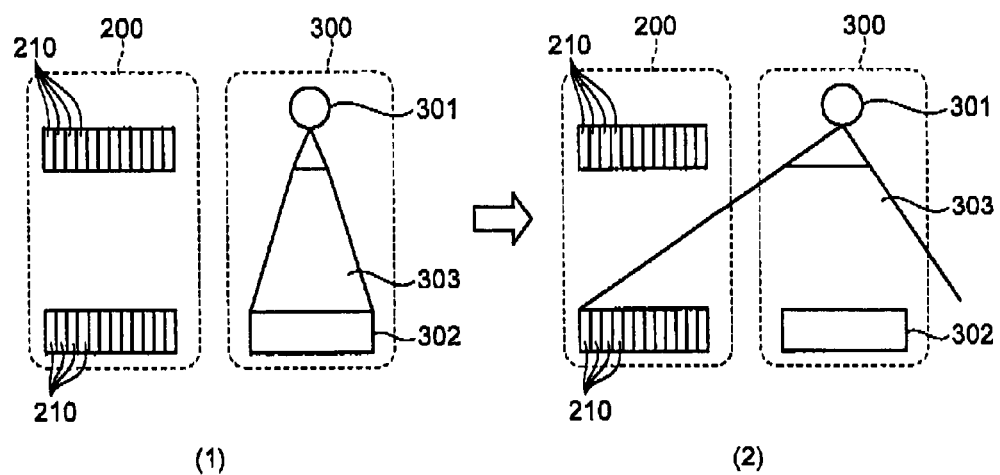
FIG. 11 is a diagram of a change in the width in which the X-ray tube emits X-rays.

For example, when the determination process is performed, the control unit 520 may adjust the collimator of the X-ray tube 301 to change the emission width of the X-ray 303. FIG. 11 is a diagram illustrating a change in the width in which the X-ray tube emits X-rays. (1) of FIG. 11 shows a state before the change in the width and (2) of FIG. 11 shows a state after the change in the width. As shown in (2) of FIG. 11, the control unit 520 increases the width in which the X-ray tube 301 emits the X-ray 303. For example, the control unit 520 increases the size of an aperture of a lens through which the X-ray tube 301 emits the X-ray 303, thereby increasing the width in which the X-ray tube 301 emits the X-ray 303. Then, the control unit 520 controls the X-ray tube 301 to emit the X-ray 303 while being rotated about the space in which the examinee 402 is arranged such that the X-ray 303 is emitted to the entire surface of the detector 210.

For example, in the above-described embodiment, the console 500 receives the count information from the PET scanner 200 and uses the received count information. However, the embodiment is not limited thereto. For example, the console 500 may receive the detection result of the detector 210 from the PET scanner 200. In this case, the console 500 receives waveform data output from the photomultiplier tube 213 and generates count information from the received waveform data.

For example, in the above-described embodiment, the console 500 receives the count information from the PET scanner 200 and generates the coincidence information. However, the embodiment is not limited thereto. For example, the PET scanner 200 may generate the coincidence information from the count information and transmit the generated coincidence information to the console 500. In this case, for example, the console 500 may determine whether there is a failure on the basis of the coincidence information received from the PET scanner 200. For example, the console 500 may receive, as information for determination, the count information or the waveform data output from the photomultiplier tube 213, separately from the coincidence information received from the PET scanner 200.

For example, in the above-described embodiment, it is determined whether the detector 210 detects the X-ray 303 emitted by the X-ray tube 301 and it is determined whether the detector 210 is out of order on the basis of the determination result. In this way, the quality of the detector 210 is checked and it is possible to reduce a load applied to the user. This point will be described in detail below. A quality test for checking whether there is a failure in the detector 210 is periodically performed. For example, the quality test for the detector 210 is performed every day. In the method according to the related art, whenever the quality test is performed every day, the phantom is input and output and it takes a lot of effort and time. In contrast, in this embodiment, it is determined whether there is a failure in the detector 210 using the X-ray 303 emitted by the X-ray tube 301. Therefore, it is not necessary to input and output the phantom every day and the time required for the quality test is reduced. In this way, the quality of the detector 210 is checked and it is possible to reduce a load applied to the user.

Among the processes in this embodiment, some or all of the processes that are automatically performed may be manually performed, or some or all of the processes that are manually performed may be automatically performed by a known method. For example, when the PET-CT apparatus 100 receives a determination instruction, the scatterer 304 may be automatically or manually arranged in the direction in which X-rays are emitted. In addition, information including the process sequence, the control sequence, the detailed names, and various kinds of data or parameters described in the specification or the drawings (FIGS. 1 to 9) may be arbitrarily changed except for special cases.

The drawings show the function and concept of the components of each apparatus, but the components of each apparatus are not necessarily physically configured as shown in the drawings. That is, the examples of the separation or integration of the apparatuses are not limited to those shown in the drawings, but some or all of the apparatuses may be functionally or physically separated or integrated in any unit according to various kinds of loads or use conditions. For example, in the above-described embodiment, the console 500 reconstructs the PET image or the X-ray CT image and then performs the determination process. However, the embodiment is not limited thereto. For example, the control unit that performs the determination process may be provided separately from the console 500. In this case, the control unit that performs the determination process may be provided outside the PET-CT apparatus 100 and may be connected to the PET-CT apparatus 100 through a network.

A radiographic program according to the above-described embodiment may be distributed through a network, such as the Internet. In addition, the radiographic program may be stored in a computer-readable recording medium, such as a hard disk, a flexible disk (FD), a CD-ROM, an MO, or a DVD, may be read from the recording medium by a computer, and may be executed.

While certain embodiments have been described, these embodiments have been presented by way of example only, and are not intended to limit the scope of the embodiments. Indeed, the novel MEDICAL IMAGING APPARATUS, control method, and computer program product described herein may be embodied in a variety of other forms; furthermore, various omissions, substitutions and changes in the form of the medical imaging apparatus, control method, and computer program product described herein may be made without departing from the spirit of the embodiments. The accompanying claims and their equivalents are intended to cover such forms or modifications as would fall within the scope and spirits of the embodiments.

According to a medical imaging apparatus of at least one embodiment described above, the medical imaging apparatus includes an X-ray tube that emits X-rays for generating an X-ray CT image; a detector that detects radiation for generating a nuclear medicine image; and a determining unit that determines whether the detector detects the X-rays emitted by the X-ray tube, thereby determining whether there is a failure in the detector. As a result, it is possible to obtain a count required to determine whether there is a failure in a short time and determine whether there is a failure in a short time.

While certain embodiments have been described, these embodiments have been presented by way of example only, and are not intended to limit the scope of the inventions. Indeed, the novel embodiments described herein may be embodied in a variety of other forms; furthermore, various omissions, substitutions and changes in the form of the embodiments described herein may be made without departing from the spirit of the inventions. The accompanying claims and their equivalents are intended to cover such forms or modifications as would fall within the scope and spirit of the inventions.

What is claimed is:

1. A medical imaging apparatus comprising:
an X-ray imaging apparatus including an X-ray tube configured to emit X-rays for generating an X-ray CT image;
a nuclear medicine imaging apparatus including a detector configured to detect radiation for generating a nuclear medicine image;
a changing unit configured to change at least one of an emission direction and an emission width of the X-rays so that the X-rays are incident on the detector; and
a determining unit configured to determine whether the detector detects the X-rays, thereby determining whether there is a failure in the detector.

2. The medical imaging apparatus according to claim 1, wherein the X-ray tube is configured to emit the X-rays while being rotated about a space in which an examinee is arranged.

3. A control method comprising:
allowing an X-ray tube to emit X-rays for generating an X-ray CT image;
allowing a detector to detect radiation for generating a nuclear medicine image;
changing at least one of an emission direction and an emission width of the X-rays so that the X-rays are incident on the detector; and
determining whether the detector detects the X-rays emitted by the X-ray tube, thereby determining whether there is a failure in the detector.

4. A non-transitory computer readable medium comprising instructions that cause a computer to execute:
allowing an X-ray tube to emit X-rays for generating an X-ray CT image;
allowing a detector to detect radiation for generating a nuclear medicine image;
determining whether the detector detects the X-rays emitted by the X-ray tube, thereby determining whether there is a failure in the detector,
wherein at least one of an emission direction and an emission width of the X-rays is changed so that the X-rays are incident on the detector.

5. The medical imaging apparatus according to claim 1, wherein the changing unit is a scatterer configured to be arranged in a direction in which the X-ray tube emits the X-rays and scatters the X-rays.

6. The medical imaging apparatus according to claim 5, wherein the scatterer is made of a metal material.

7. The medical imaging apparatus according to claim 5, wherein the scatterer is a sphere.

8. The medical imaging apparatus according to claim 5, wherein the scatterer is a polyhedron.

9. The medical imaging apparatus according to claim 5, wherein the scatterer has an angle such that the X-ray is not scattered to outside of the detector.

10. The medical imaging apparatus according to claim 1, wherein the changing unit is a collimator of the X-ray tube.

* * * * *